United States Patent
Coufal

(10) Patent No.: US 6,790,956 B1
(45) Date of Patent: Sep. 14, 2004

(54) METHOD FOR PRODUCING PURE MELAMINE

(75) Inventor: Gerhard Coufal, Leonding (AT)

(73) Assignee: Agrolinz Melamin GmbH, Linz (AT)

( * ) Notice: Subject to any disclaimer, the term of this patent is extended or adjusted under 35 U.S.C. 154(b) by 0 days.

(21) Appl. No.: 09/830,074

(22) PCT Filed: Nov. 5, 1999

(86) PCT No.: PCT/EP99/08462

§ 371 (c)(1), (2), (4) Date: Apr. 23, 2001

(87) PCT Pub. No.: WO00/29393

PCT Pub. Date: May 25, 2000

(30) Foreign Application Priority Data

Nov. 13, 1998 (AT) .............................................. 1894/98

(51) Int. Cl.$^7$ ............................................ C07D 251/62
(52) U.S. Cl. ...................................... 544/203; 544/201
(58) Field of Search ................................ 544/203, 201, 544/207

(56) References Cited

U.S. PATENT DOCUMENTS

| | | | | |
|---|---|---|---|---|
| 3,386,999 A | * | 6/1968 | Manes ...................... | 260/249.7 |
| 3,637,686 A | * | 1/1972 | Kokubo et al. .......... | 260/249.7 |
| 4,408,046 A | * | 10/1983 | Van Hardeveld ............ | 544/201 |
| 5,721,363 A | | 2/1998 | Canzi et al. ................. | 544/201 |

FOREIGN PATENT DOCUMENTS

| | | |
|---|---|---|
| AU | 709030 | 6/1997 |
| CN | 1171102 | 1/1998 |
| WO | 96/20182 | 7/1996 |
| WO | 96/23778 | 8/1996 |
| WO | 97/20826 | 6/1997 |

OTHER PUBLICATIONS

Elvers et al. Ullmann's Encyclopedia of Industrial Chemistry, 5th Edition, vol A16, 174–179, 1978.*

* cited by examiner

Primary Examiner—Richard L. Raymond
Assistant Examiner—Venkataraman Balasubramanian
(74) Attorney, Agent, or Firm—Wenderoth, Lind & Ponack LLP

(57) ABSTRACT

The invention relates to a method for producing pure melamine. According to this method, the melamine melt, which is produced from urea in a high-pressure process, is cooled and ammonia is added until it reaches a temperature of approximately 1 to 50° C. above the melting temperature of the melamine as dependent on the respective pressure of ammonia and then either a) quenched with water or an aqueous solution or suspension containing ammonia and/or melamine so that the melamine solidifies or b) quenched with cold liquid or gaseous ammonia, so that the melamine solidifies, the melamine then being cooled further with water or an aqueous solution or suspension containing ammonia and/or melamine and c) the melamine is then isolated.

12 Claims, No Drawings

METHOD FOR PRODUCING PURE MELAMINE

The invention relates to a method for producing pure melamine in a high-pressure process in which, before solidification, the melamine melt is cooled with a supply of ammonia and is then worked up in an aqueous medium. The production of melamine by pyrolysis of urea is known, for example, from "Ullmann's Encyclopedia of Industrial Chemistry, Vol. A16, 5$^{th}$ ed (1990), pages 171–185. In the Montedison process described therein by way of example, urea is decomposed in a reactor at 370° C. and 70 bar together with ammonia in the course of 20 min. The reaction mixture substantially comprising a melamine melt, ammonia and $CO_2$ is then depressurized to 25 bar in a quencher and is treated at 160° C. with an aqueous $NH_3/CO_2$ solution, solid melamine being precipitated. In order to decompose any unconverted urea or byproducts, the crude melamine suspension obtained is, if required, left in the quencher for some time. Thereafter, the melamine suspension is, if required, freed from $NH_3$ and $CO_2$ in a stripper and diluted by adding mother liquor, the melamine being dissolved. After the addition of sodium hydroxide solution and treatment with active carbon, the melamine is crystallized.

In a further melamine process (Nissan process), the urea decomposition is effected at 100 bar and 400° C., the urea melt employed being used before the melamine synthesis for washing melamine and urea out of the off-gases of the melamine reactor. The melamine melt obtained is quenched with an aqueous ammonia solution, optionally after an ageing step, is dissolved thereby and is left to dwell at 180° C. for decomposition of impurities. After stripping of the ammonia and filtration of the solution, the melamine is crystallized. According to U.S. Pat. No. 3,637,686, the melamine melt, before being quenched with aqueous ammonia, is quenched in a first step with cold liquid or gaseous ammonia at a pressure of from 5 to 100 bar and a temperature from 200 to 270° C., the melamine solidifying.

The crude melamine initially obtained in the melamine synthesis, which contains from about 94 to 97% by weight of melamine, depending on the production process, and in particular melam, melem, melone, ureidomelamine, ammeline and ammelide as substantial impurities, is however unsuitable or only insufficiently suitable for most applications owing to the inadequate quality of the resins preparable therewith. In order to obtain a pure melamine, additional process steps, such as, for example, recrystallization, are necessary.

It is accordingly the object to provide a simpler method by means of which melamine can be obtained in better purity and with good yields. According to the invention, this object could be achieved if the crude melamine melt arriving from the melamine reactor is cooled to just above the melting point before solidification and aqueous working-up with incorporating further ammonia.

The present invention accordingly relates to a method for producing pure melamine, characterized in that the melamine melt prepared from urea in a high-pressure process, optionally after stripping of the off-gases and optionally after dwelling in an ageing container, is cooled to a temperature which is about 1 to 50° C. above the melting point of melamine dependent on the respective ammonia pressure, with the addition of ammonia, after which either a) quenching is effected with water or an aqueous ammonia- and/or melamine-containing solution or suspension and the melamine is solidified - or b) quenching is effected with cold liquid or gaseous ammonia, the melamine solidifying and then being further cooled in a second step with water or an aqueous ammonia- and/or melamine-containing solution or suspension and c) the melamine is then isolated.

In melamine high-pressure processes, melamine is obtained in liquid form as a melt at pressures of from about 70 to 800 bar and temperatures of at least about 370° C. The off-gases formed in the melamine synthesis and containing in particular $NH_3$ and $CO_2$ can be separated off either before or after cooling of the melt. Advantageously, the off-gases are washed by being passed through a urea melt, in particular particles of melamine or of unconverted urea which are entrained by the off-gases being washed out. The urea melt is heated by the hot off-gases and is advantageously passed into a melamine reactor for melamine synthesis, while the purified off-gases are advantageously passed into a urea reactor. Either the off-gases can be passed directly into the urea reactor or they are condensed, for example with the aid of ammonium carbonate or ammonium carbamate solutions which are obtained, for example, in the melamine plant or the urea plant. The resulting heat can be used, for example, for preheating the ammonia used in the urea plant or for the production of steam.

After the off-gases have been separated off, the melamine melt can advantageously be stripped, for example with $NH_3$, with the result that in particular residual $CO_2$ is removed. It is furthermore advantageous to allow the melamine melt to dwell in an ageing container, as described, for example, in WO96/23778 or WO96/20182. The cooling according to the invention to the temperature of about 1 to 50° C. above the melting point of melamine which is dependent on the respective ammonia pressure can be effected either by means of heat exchangers or by feeding cold liquid, gaseous or supercritical $NH_3$ into the gas space above the melt or preferably by passage into the melt or by a combination of these cooling measures, thorough mixing, for example by passing in $NH_3$, possibly by additional mixing means, such as, for example, stirrers, static mixers, etc., being advantageous. Ideally, a melamine melt saturated with $NH_3$ is obtained. According to the invention, however, melamine melts supersaturated or subsaturated with $NH_3$ can also be obtained at the respective pressure and the respective temperature, depending on the process conditions and on the amount of $NH_3$ fed in. The melt is preferably cooled to a temperature which is about 1 to 30° C. above the melting point of the melamine which is dependent on the respective ammonia pressure. It has proved particularly advantageous if cooling is effected to a temperature which is as close as possible above the melting point of melamine which is dependent on the respective ammonia pressure. Preferably, the cooling is effected over a period of from about 1 min to 10 h, particularly preferably from about 1 min to 1 h. The dwell time in this temperature range is from about 1 min to 10 h, preferably from about 1 min to 1 h. The ammonia pressure during the cooling is preferably from about 50 to 1000 bar, pressures of from about 50 to 400 bar being particularly preferred. It is advantageous if a pressure increase is simultaneously effected by means of the ammonia feed.

The melt can be cooled, for example, in the ageing container or in a separate suitable container or heat exchanger. The quenching carried out after the cooling of the melt is effected by mixing the cooled melamine melt with water or an aqueous solution or suspension (according to a) or with ammonia and then with water or an aqueous solution or suspension (according to b). The mixing is carried out particularly advantageously and thoroughly by spraying or passing the individual substances, or by spraying or passing the melt, into the initially introduced solution or suspension with simultaneous pressure reduction. For quenching of the melamine melt in stage a), particularly advantageously and economically the mother liquor obtained in the solidification or crystallization and isolation of the melamine can be recycled and reused. The temperature during quenching of the melamine melt with water or with an aqueous ammonia- and/or melamine-containing solution or suspension according to step a) is preferably from about 25 to 300° C., particularly preferably from about 50 to 200° C., and the pressure is from about 1 to 100 bar, particularly preferably from about 1 to 50 bar. The temperature is dependent on the operating conditions in the quencher, in particular on pressure, concentrations and flow rates. The quenching according to b) with ammonia is preferably effected at from about 200 to 270° C. and a pressure from about 1 to 100 bar, particularly preferably from about 1 to 50 bar, after which, in a second cooling step, further cooling is effected with water or an aqueous ammonia- and/or melamine-containing solution or suspension, preferably to about 50 to 200° C. The crystallized or solidified melamine obtained during the cooling is then isolated by separating off the mother liquor, for example by filtration or centrifuging, and is then dried, melamine being obtained in good yield and with good purity in the region of about 99%, owing primarily to the omission of further purification steps.

The quenching is advantageously carried out continuously in a quench container downstream of the cooling of the melt. For example, liquid melamine enters the upper part of the quench container at a temperature which is from just above the melting point, which is dependent on the respective ammonia pressure, to about 370° C. and a pressure of from about 100 to 400 bar and is quenched both with water and with the recycled aqueous suspension of solid melamine in an aqueous melamine solution from the quench container or the recycled mother liquor, which are likewise sprayed into the top of the quench container. The water sprayed in has, for example, a temperature of from about 25 to 90° C. and the suspension or mother liquor sprayed in has a temperature from about 25 to 150° C. at a pressure of from about 1 to 10 bar. According to this example, the temperature in the quench container is kept approximately constant, the melamine suspension in the quench container is advantageously stirred, that part of the melamine suspension which is not recycled and which, in addition to solid melamine, also contains dissolved melamine and ammonia is taken off continuously from the lower part of the quench container, the melamine is isolated by filtration or centrifuging and is dried and the mother liquor is partly recycled and partly removed.

In order to achieve higher and very high purities, the melamine can be recrystallized. It is also possible for the melamine obtained according to a) or b) to be dissolved, without prior isolation, directly in the suspension by feeding in an aqueous ammoniacal solution, particularly preferably and economically the mother liquor obtained during this solidification or crystallization of the melamine being recycled and being used for the dissolution. Any byproducts formed by hydrolysis, especially the oxyaminotriazines, such as, for example, ammeline and ammelide, can, if required, be kept in solution by adding an alkali, for example NaOH. The solution is, if required, allowed to dwell, if required dissolved $NH_3$ is also stripped off and, if required, treatment with active carbon is effected. This is followed by filtration, and the melamine is crystallized, for example by further cooling and/or reduction of the pressure or application of a vacuum, and is separated from the mother liquor and dried.

The melamine obtained according to the present invention has a higher purity compared with conventional melamine after quenching with water, and the yield after the recrystallization is higher.

After the drying, the melamine can be aged for further improvement of the quality. The isolated, optionally recrystallized melamine is allowed to dwell (tempering), preferably under $NH_3$ pressure of from about 5 to about 600 bar, preferably from about 5 to 100 bar, and at a temperature of from about 100° C. to below the melting point of the melamine which is dependent on the respective $NH_3$ pressure, for a period of from about 5 min to 10 h, preferably from about 5 min to 5 h.

EXAMPLE 1

20 g of melamine having a melam content of 2% by weight and a melem content of 1% by weight were introduced into an autoclave having a volume of 100 ml, and the autoclave was brought to a temperature of 370° C. with an $NH_3$ feed at an $NH_3$ pressure of 250 bar and was kept at this temperature and this pressure for 2 h. Cooling was then effected to 320° C. in the course of 1 h with an $NH_3$ feed, the pressure of 250 bar being maintained, this temperature was maintained for 30 min and the melamine melt was then sprayed into a second autoclave (1000 ml volume) in which an aqueous ammonia solution at a temperature of 159° C. and a pressure of 12 bar was present. The melamine solidified and the temperature in the second autoclave increased to 168° C. and the pressure to 24 bar. After cooling of the autoclave, filtration and drying, melamine having a purity of 99.1% was obtained.

EXAMPLE 2

20 g of melamine having a melam content of 2% by weight and a melem content of 1% by weight were introduced into an autoclave having a volume of 100 ml, and the autoclave was brought to a temperature of 370° C. with an $NH_3$ feed at an $NH_3$ pressure of 250 bar and was kept at this temperature and this pressure for 2 h. Cooling was then effected to 330° C. in the course of 1 h with an $NH_3$ feed, the pressure of 250 bar being maintained, this temperature was maintained for 30 min and the melamine melt was then sprayed into a second autoclave (1000 ml volume) in which an aqueous ammonia solution at a temperature of 62° C. and a pressure of 1 bar was present. The melamine solidified and the temperature in the second autoclave increased to 81° C. and the pressure to 4 bar. After cooling of the autoclave, filtration and drying, melamine having a purity of 98.8% was obtained.

EXAMPLE 3

20 g of melamine having a melam content of 2% by weight and a melem content of 1% by weight were introduced into an autoclave having a volume of 100 ml, and the autoclave was brought to a temperature of 370° C. with an $NH_3$ feed at an $NH_3$ pressure of 250 bar and was kept at this temperature and this pressure for 2 h. Cooling was then effected to 350° C. in the course of 1 h with an $NH_3$ feed, the pressure of 250 bar being maintained, this temperature was maintained for 30 min and the melamine melt was then sprayed into a second autoclave (1000 ml volume) in which an aqueous ammonia solution at a temperature of 63° C. and a pressure of 1 bar was present. The melamine solidified and the temperature in the second autoclave increased to 88° C. and the pressure to 4 bar. After cooling of the autoclave, filtration and drying, melamine having a purity of 98.6% was obtained.

COMPARATIVE EXAMPLE 1

20 g of melamine having a melam content of 2% by weight and a melem content of 1% by weight were introduced into an autoclave having a volume of 100 ml, and the autoclave was brought to a temperature of 370° C. with an $NH_3$ feed at an $NH_3$ pressure of 250 bar and this temperature and this pressure was maintained for 2 h. The melamine melt was then sprayed into a second autoclave (1000 ml volume) in which an aqueous ammonia solution having a temperature of 62° C. and a pressure of 1 bar was present. The melamine solidified and the temperature in the second autoclave increased to 94° C. and the pressure to 5 bar. After cooling of the autoclave, filtration and drying, melamine having a purity of 97.5% was obtained.

What is claimed is:

1. A method for producing pure melamine wherein the melamine melt prepared from urea in a high-pressure process, optionally after stripping of the off-gases and optionally after dwelling in an ageing container, is cooled to a temperature which is about 1 to 50° C. above the melting point of melamine dependent on the respective ammonia pressure, with the addition of ammonia, after which quenching is effected with water or an aqueous ammonia- and/or melamine-containing solution or suspension and the melamine is solidified and isolated.

2. The method according to claim 1, wherein the cooling of the melamine melt to the temperature which is from about 1 to 50° C. above the melting point of the melamine is effected by passing in cold liquid or gaseous ammonia.

3. The method according to claim 1, wherein the melamine obtained and present as a suspension is dissolved by feeding in an aqueous ammoniacal solution, the solution is optionally mixed with NaOH and, optionally, allowed to dwell, the dissolved ammonia is, optionally, stripped, filtration is then effected and the melamine is crystallized and isolated.

4. The method according to claim 1, wherein the melamine melt is quenched by means of recycled mother liquor obtained in the crystallization.

5. The method according to claim 1, wherein the melamine melt is cooled to a temperature which is from about 1 to 50° C. above the melting point of the melamine, at an ammonia pressure of from about 50 to 1000 bar while feeding in ammonia.

6. The method according to claim 1, wherein the melamine melt is cooled to a temperature which is from about 1 to 30° C. above the melting point of the melamine.

7. The method according to claim 1, wherein the melamine melt is cooled to a temperature which is from about 1 to 50° C. above the melting point of the melamine, by passing in ammonia for from about 1 minute to 10 hours.

8. The method according to claim 1, wherein quenching is effected at a temperature of from about 25° C. to 300° C., and a pressure of from abut 1 to 100 bar.

9. The method according to claim 1, wherein the melamine and urea are washed out of the off-gases of the melamine reactor by means of a urea melt which simultaneously heats up, and the urea melt is then fed to the melamine synthesis in a melamine reactor and the off-gases are fed to a urea reactor.

10. The method according to claim 9, wherein the off-gases freed from melamine and urea are condensed, optionally with the aid of ammonium carbonate solution and/or ammonium carbamate solution which are taken off from a urea plant or the melamine plant, and the resulting heat is used for preheating the liquid ammonia used in the urea plant or for the production of steam.

11. The method according to claim 3, wherein the aqueous ammoniacal solution is a recycled mother liquor obtained in the crystallization.

12. The method according to claim 8, wherein the quenching temperature is from about 50° C. to 200° C. and the pressure is from about 1 to 50 bar.

* * * * *